(12) United States Patent
Wakabayashi (10) Patent No.: US 6,299,593 B1
(45) Date of Patent: Oct. 9, 2001

(54) DOUBLE AND MULTIPLE LUMEN CHEST DRAINAGE TUBE

(76) Inventor: Akio Wakabayashi, 1200 N. Tustin Ave., Suite 105, Santa Ana, CA (US) 92705

( * ) Notice: Subject to any disclaimer, the term of this patent is extended or adjusted under 35 U.S.C. 154(b) by 0 days.

(21) Appl. No.: 09/518,472

(22) Filed: Mar. 3, 2000

(51) Int. Cl.[7] .................................................. A61M 31/00

(52) U.S. Cl. ............................................................. 604/48

(58) Field of Search .................................. 604/48, 43, 30, 604/31, 523, 27, 533, 534, 515, 535, 537, 284, 264

(56) References Cited

U.S. PATENT DOCUMENTS 4,182,343 * 1/1980 Inaba .................................. 128/350 R
4,555,242 * 11/1985 Saudagar .................................. 604/96

* cited by examiner

Primary Examiner—Manuel Mendez
(74) Attorney, Agent, or Firm—Willie Krawitz (57) ABSTRACT

A double-lumen chest drainage tube is employed to remove a mixture of air, blood and fluids from a pleural cavity following lung surgery. The drainage tube is constructed of a polymeric inner tube having large but few aspirating perforations surrounded by a connected, spaced-apart, outer tube defining numerous smaller perforations. The outer and inner tubes are separated by septa to prevent collapse of the tubes. When a relatively high suction pressure is applied to the inner tube, the suction pressure is transmitted through the large, few perforations in the inner tube to the space between the two tubes, where the negative aspirating pressure is to be equalized and evenly distributed. When this equalized aspirating pressure is transmitted to the numerous small perforations of the outer tube to the pleural cavity, the negative pressure per square centimeter becomes considerably reduced due to a substantially increased surface area of these numerous, small perforations of the outer tube. of it will become evenly distributed. This will reduce the possibility of sucking the lung or soft tissues onto the chest drainage tube and blocking the tube perforations. Multiple double lumen tubes can be bonded together using thin, polymeric severable membranes with a single common connector being attached to one end of the tubes. After the double lumen tubes are inserted into the chest cavity through a single entry in the chest wall, they can be severed to form individual double lumen tubes which can be positioned to drain various sites inside the chest cavity. The reduction of insertion sites lessens the possibility of potential chest tube site infections.

18 Claims, 7 Drawing Sheets

DOUBLE AND MULTIPLE LUMEN CHEST DRAINAGE TUBE

BACKGROUND OF THE INVENTION

This invention relates to a new and improved drainage device for the chest cavity following lung surgery, and which will remove air, fluid, blood and blood clots from the chest cavity. Drainage tubes for open heart surgery typically use a single lumen drainage tube with large perforations connected to a vacuum source. These drainage tubes are used in patients after lung surgery, as well.

However, different post operative conditions prevail following heart and lung surgery. For example in the case of heart surgery, an accurate measure of bleeding and effective drainage of blood and blood clots to prevent compression on the heart (tamponade) is one of the most important features of a chest drainage tube. Also, in the case of heart surgery, venting or leaking air from the lung dues not represent a critical factor in the design of a chest tube.

By contrast in the case of lung surgery, an air leak from the chest cavity is always a major problem, particularly for lung volume reduction surgery of emphysematous lungs. Also, the measurement of blood loss following lung resection is generally not as critical compared to open heart surgery, since the amount of blood loss is small.

Another problem following lung surgery is that drainage tubes commonly used in both lung and heart surgery employ a few large round or elliptically-shaped holes (5–10 mm diameter), and these large hole sizes are required to remove blood and/or clots. These holes may become blocked when a suction pressure such as 15 torr is applied to the drainage tube causing the lung or other soft tissue inside the chest cavity to be sucked against the device.

Despite these major differences, the same chest drainage tube is used for both open heart and lung resection surgeries because the number of open heart surgeries far exceeds those of lung surgeries; hence, no chest drainage tube is presently available which is specifically geared for use following lung surgery.

Another problem associated with the use of chest drainage tubes is that following heart and lung surgery, air in the chest cavity tends to rise and blood/fluids tend to descend, and hence two chest tubes are routinely placed at high and low points in the chest cavity. However, if an air leak from the lung persists for more than a few days, the lung becomes adhered to the chest wall, creating isolated spaces around the lung. The development of these loculated air spaces which do not communicate with installed chest tubes is not uncommon. To circumvent this problem, some surgeons place three chest tubes through the chest wall using three separate small incisions. But, since each chest tube insertion site represents a potential source of wound infection, three skin incisions pose a three fold greater risk of a wound infection. Hence, it would be desirable to reduce the number of skin incisions and a corresponding reduction in the risk of infection.

A three-in-one, (or other multiple) drainage device embodiment of this invention would represent a considerable improvement over conventional multiple chest tube insertions. A three-in-one drainage device, for example, would reduce the possibility of infection at multiple insertion sites since only a single incision at the insertion site would be involved. There would also be reduced the amount of dressing gauze and adhesive tape which can cause skin irritation.

Various types of suction catheters, drainage catheters and filters are disclosed in U.S. Pat. Nos. 2,112,666; 3,308,825; 3,520,300; 3,623,483; 3,785,380; 3,810,471; 3,903,895; 4,068,664; 4,256,102; 4,398,910; 4,493,707; 4,601,697; 4,619,643; 4,692,153; 4,767,404; 5,045,075; 5,348,788; 5,370,610; and, 5,578,006. However, these patents do not disclose an effective means for removing air, blood and/or blood clots from a chest cavity surgical site with reduced problems due to aspiration or ingestion of lung or other tissue against or into the drainage device itself.

THE INVENTION

According to the invention, a drainage device for a chest cavity comprises a double lumen catheter constructed with an inner tube defining relatively few large perforations (e.g., elliptically shaped) and an outer tube with numerous, smaller perforations for primarily venting air and liquid such as bloody pleural effusion at a relatively high suction pressure. The inner and outer tubes are separated by septa, which prevent collapse of the outer tube. When suction is applied to the inner tube, a high negative pressure (e.g., 15–25 torr) at each perforation is transmitted to the space between the outer and inner tubes where the negative pressure is reduced, equalized and evenly distributed. Since the total surface area of the small perforations of the outer tube can be sized to be considerably greater than that of the few large perforations of the inner tube, the pressure at each small perforation of the outer tube can be considerably reduced.

Hence, the combination of significantly lower suction pressure per square centimeter and substantially greater number of perforations of the outer tube will reduce the possibility that lung or other soft tissue inside the chest cavity will be sucked against the chest tube. Consequently, there will be a reduced possibility that the small, venting perforations of the outer tube will become blocked.

In a further embodiment of the invention, two or more individual drainage devices may be combined into a single device, each individual drainage device being separated by a tear strip. Following insertion of the combined drainage device into a single insertion site, the individual drainage devices are separated and then moved to different locations in the chest cavity, thereby reducing problems associated with a plurality of insertion sites.

DESCRIPTION OF THE PREFERRED EMBODIMENTS

Figure 1:
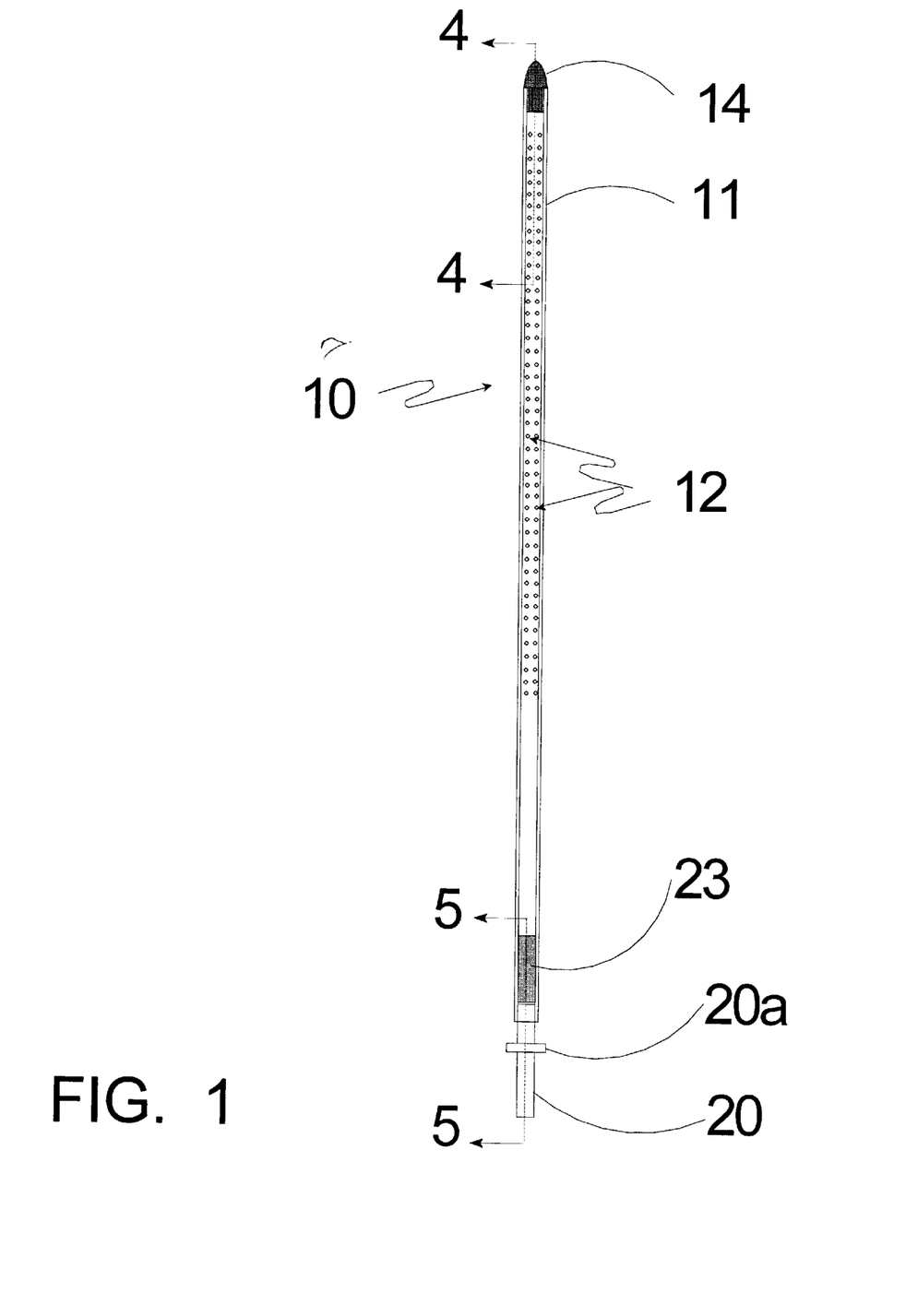
FIG. 1 is a plan view of a double lumen drainage device, according to the invention.
Figure 2:
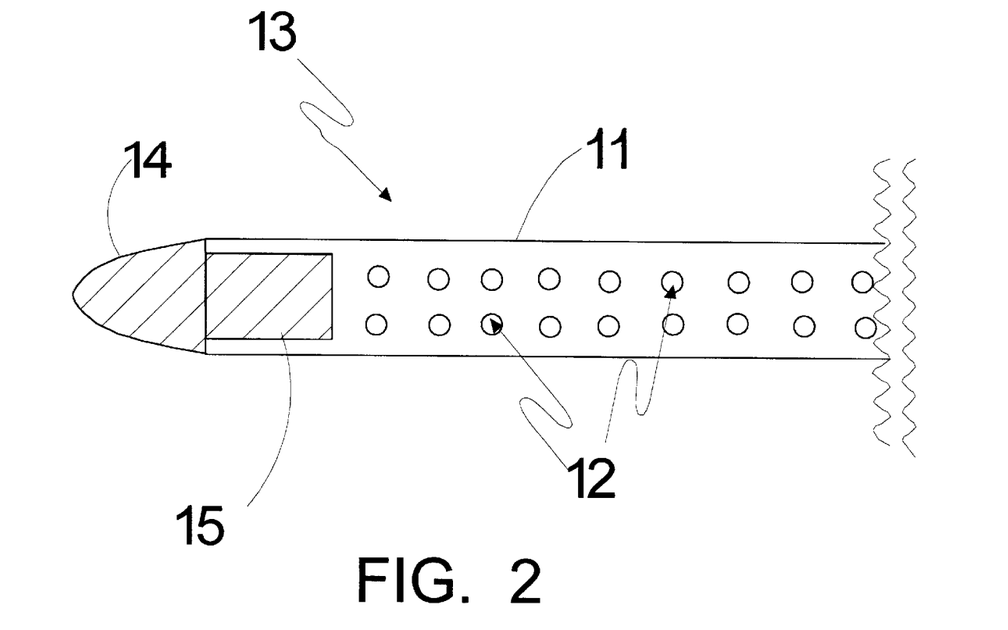
FIG. 2 is an enlarged plan view of the outer tube near the distal end of the drainage device.
Figure 3:
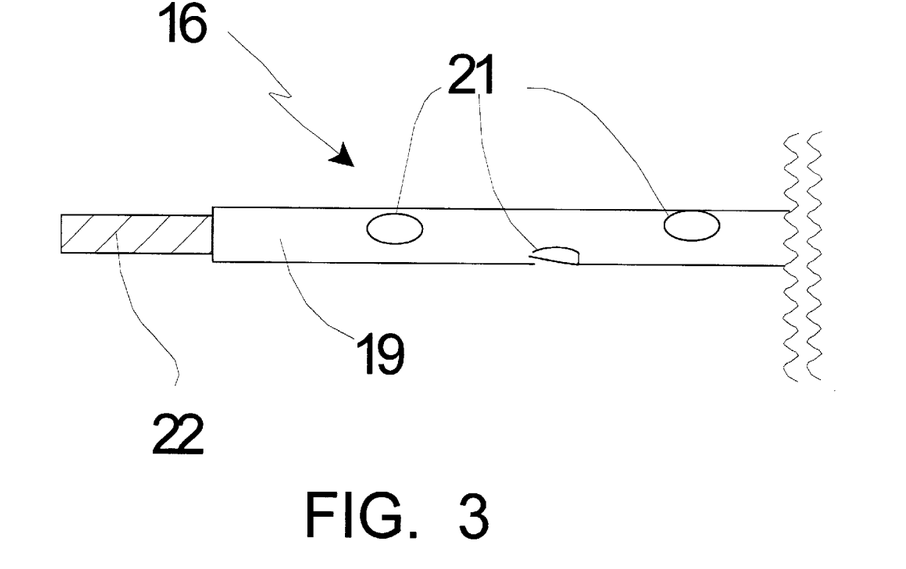
FIG. 3 is a view in longitudinal, axial section of the inner tube near the distal end of the drainage device.

A single, double-lumen drainage device 10 is shown assembled in FIGS. 1–3, and provides a square-shaped outer tube 11 and a round inner tube 19. Both inner and outer tubes are constructed of a biocompatable polymer such as, but not limited to, PVC or silastic rubber. The distal end 13 of the device 10 shown in FIG. 2 provides a solid, elliptically-shaped radiopaque tip 14 to facilitate entry into a patient's chest cavity. A connector 20 with a flange 20a is inserted into proximal end 18 (FIG. 5) of the outer tube 11. A solid filling material 23 such as plastic is inserted between outer tube 11 and inner tube 19 near the proximal end 18 and is viewable through the transparent outer tube 11.

An enlarged view of the distal end 13 of drainage device 10 is shown in FIG. 2, and illustrates a plurality of small round perforations 12 and a radiopaque filling material 15 at the distal end 13, and is viewable through transparent outer tube 11. An enlarged view of the distal end 16 of the inner tube 19 in FIG. 3 illustrates a series of large, round or elliptically-shaped perforations 21 along the inner tube 19 and end plug 22.

Figure 4:
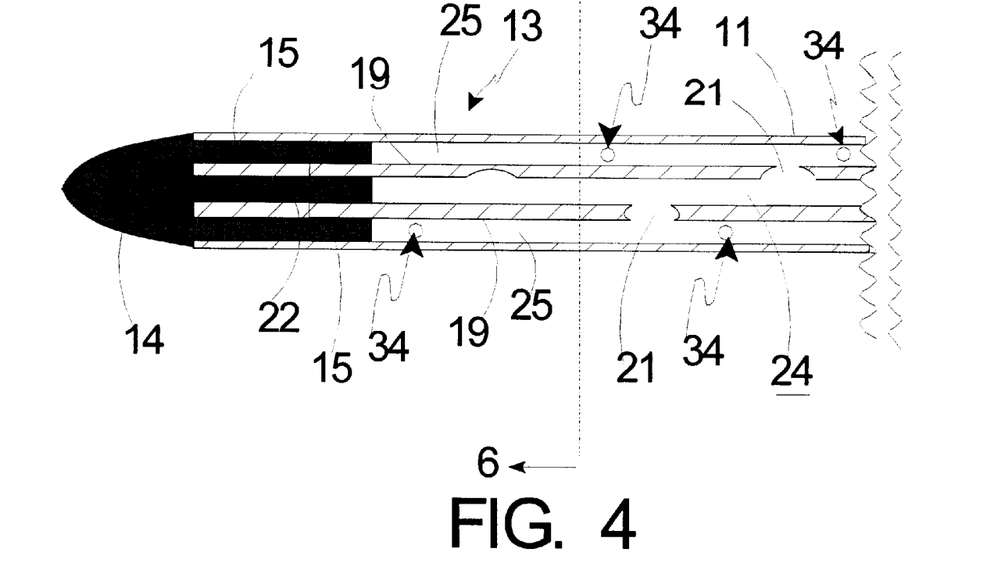
FIG. 4 is a longitudinal view in axial section near the distal end of the drainage device taken lines 4—4 of FIG. 1.
Figure 5:
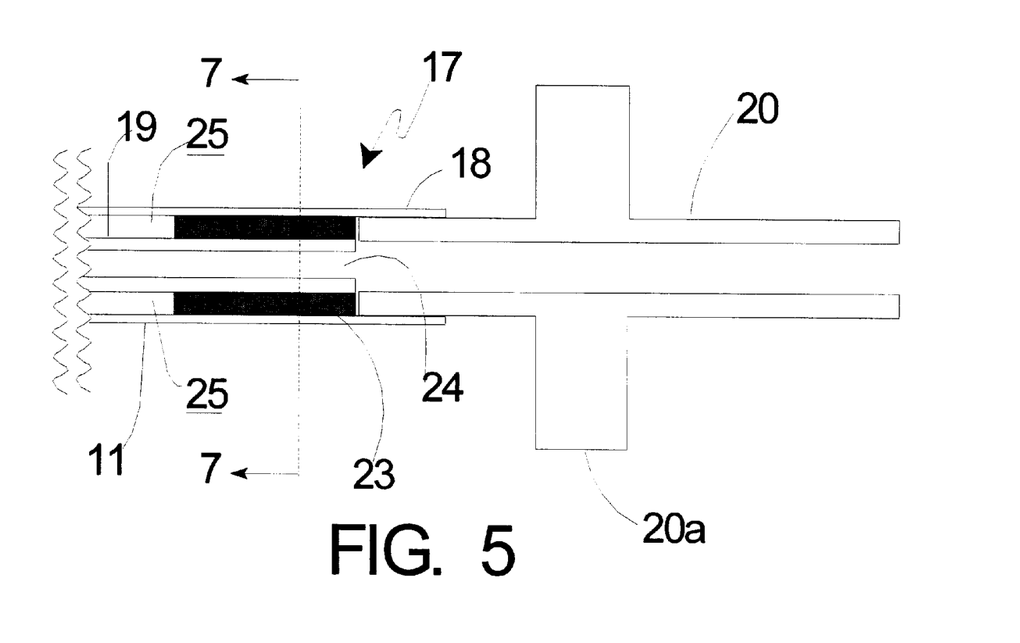
FIG. 5 is an enlarged, plan view of the inner tube near the distal end, taken along lines 5—5 of FIG. 1.
Figure 6:
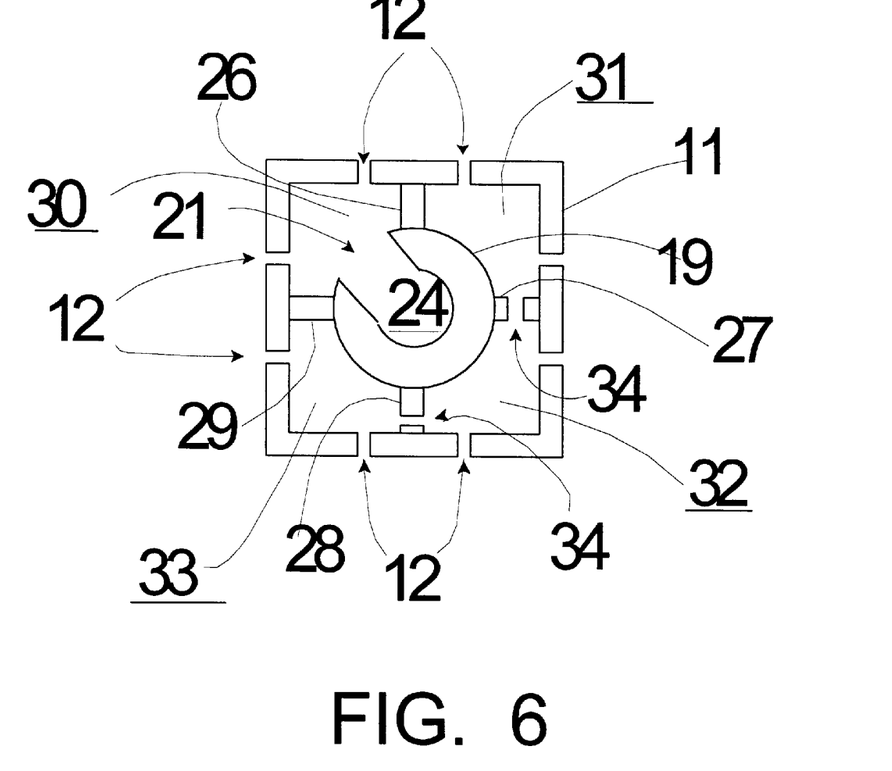
FIG. 6 is an enlarged cross section view of the drainage device taken along lines 6—6 of FIG. 4.
Figure 7:
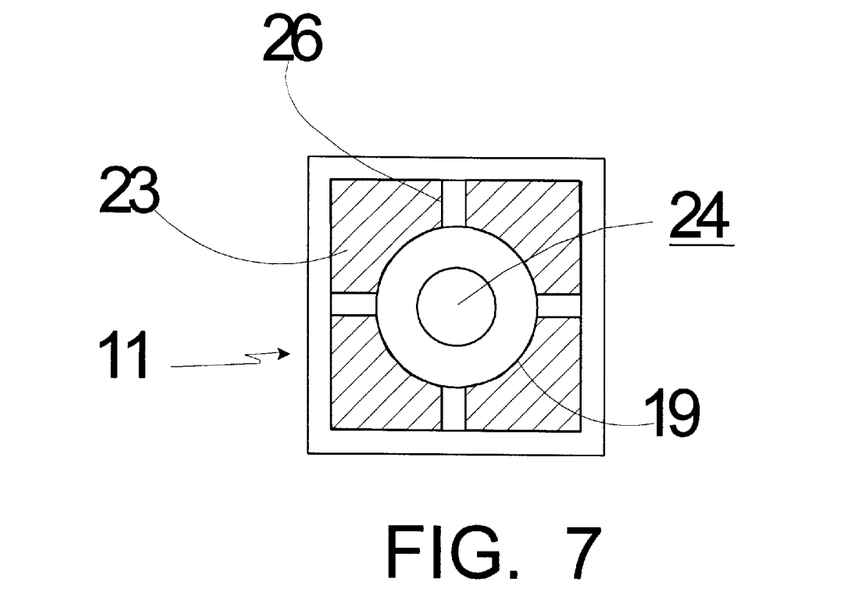
FIG. 7 is an enlarged cross section view in axial section taken along lines 7—7 of FIG. 5.

The radiopaque material 15 fills the distal tip of an elongate, circumferential space 25 between the outer tube 11 and the inner tube 19, as shown in FIG. 4. Also, FIG. 4 illustrates a central bore 24 of the inner tube 19 which is packed with the radiopaque end plug 22 at the distal tip. A plurality of septa 26, 27, 28 and 29 bridge the outer tube 11 and inner tube 19 and define a series of small round perforations 34 shown in FIG. 6. The circumferential space 25 between the outer and inner tubes 11 and 19 at the proximal end 17 of the drainage device is partially filled with the solid material 23 (FIGS. 5 and 7). The proximal end 18 of the outer tube 19 extends beyond inner tube 19 to facilitate insertion of connector 20 (FIG. 5). The inner tube 19 defines a central suction bore 24 extending along the inner tube.

As will be described, infra, the septa 26–29 are mounted within the circumferential space 25 to prevent collapse of the outer tube when suction pressure is applied. The proximal end 18 of the drainage device is sized for insertion of the suction connector 20 and flange 20a for attachment to a suction source (not shown). The inner tube 19 defines a central suction bore 24 extending along the length of the inner tube.

As will be described, infra, the septa 26–29 are mounted within the circumferential space 25 (dotted designation) and function to prevent collapse of the outer tube when suction pressure is applied. FIGS. 6 and 7 indicate the circumferential space 25 between the outer tube 11 and inner tube 19 is divided into a plurality (e.g. four) of chambers 30, 31, 32 and 33 by the septa 26, 27, 28 and 29. The septa are mounted within the space 25 and extend axially along the space to prevent collapse of the inner and outer tubes into each other. The chambers 30–33 communicate with each other via the series of perforations 34 (about 1–1½ mm in diameter) defined by the septa. The central bore 24 of the inner tube 19 communicates with the space 25 via the round or elliptical perforations 21.

Since, the proximal portion of the circumferential space 25 between the outer tube 11 and inner tube 19 is filled with the solid, plastic material 23, this will reduce the overall volume of the space 25, and at the same time the solid material provides additional support between the inner and outer tubes; hence, only the central bore 24 of the inner tube 19 remains open.

Given a drainage tube 35 cm. long and 8.5 mm. wide, and a perforation size of about 1 mm. in diameter, for 8 lines of perforations 12, each line having 47 perforations, a total surface perforation area of about 295 mm$^2$ will be formed in outer tube 11. Similarly, five elliptically-shaped perforations 21 (4.0×2.0 mm$^2$) of the inner tube will form a total surface perforation area of about 100 mm$_2$. Hence, when suction pressure is applied to the inner tube 19, this negative pressure is transmitted to the four chambers 30–33 through perforations 21 of the inner tube, where high negative pressure is reduced and evenly distributed inside the circumferential space 25. This will reduce the suction pressure per square centimeter to about 100/295, or about ⅓ at the smaller, round perforations 12 of the outer tube. Hence, the considerably lower suction pressure per square centimeter at the perforations 12 of the outer tube, will significantly reduce the possibility that lung or other soft tissues inside the chest cavity will be sucked against these perforations, thereby lessening the possibility that the perforations of the outer tube will become blocked.

Figure 8:
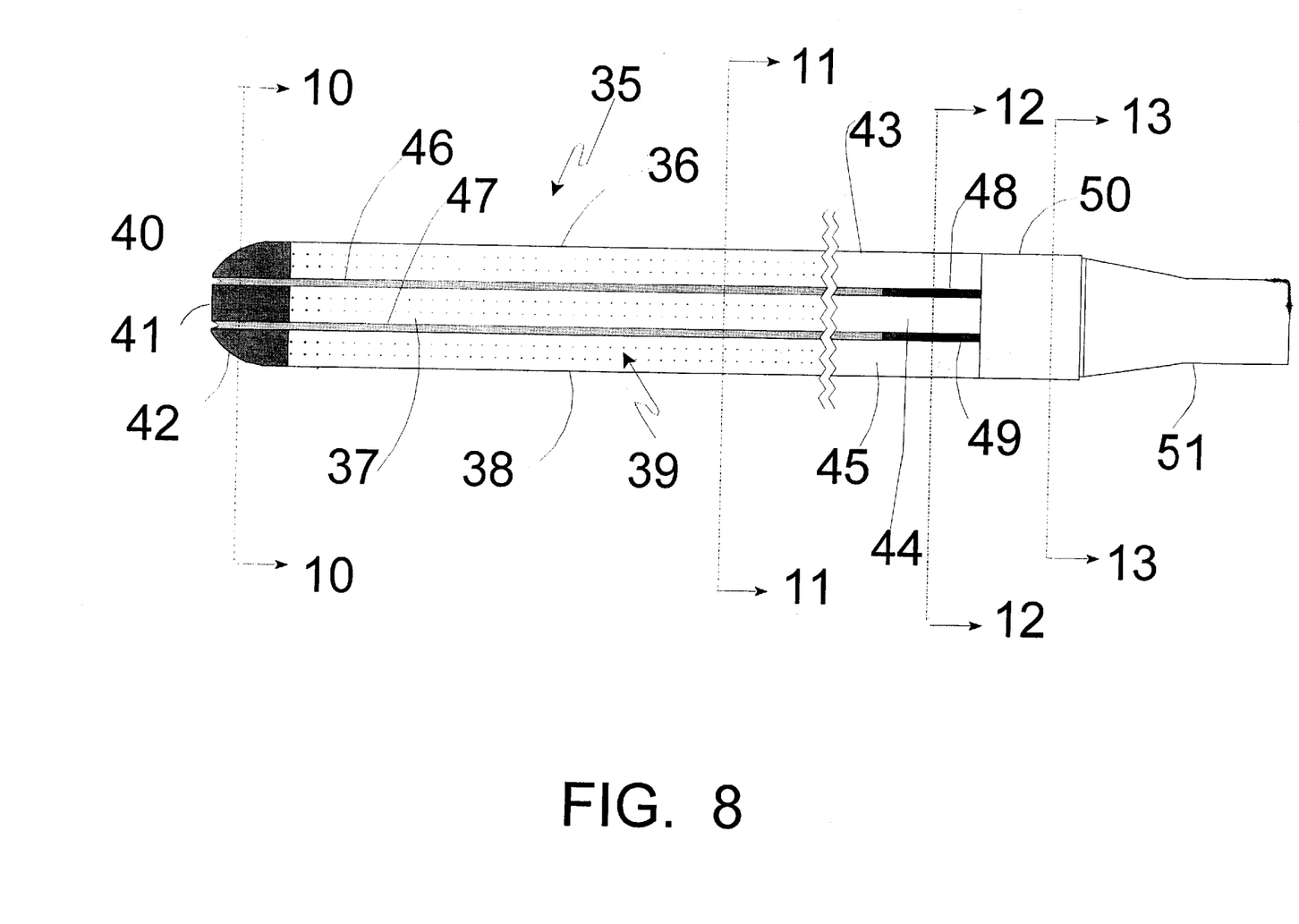
FIG. 8 is a plan view of a multiple (three-in-one), double lumen drainage device, according to the invention.
Figure 9:
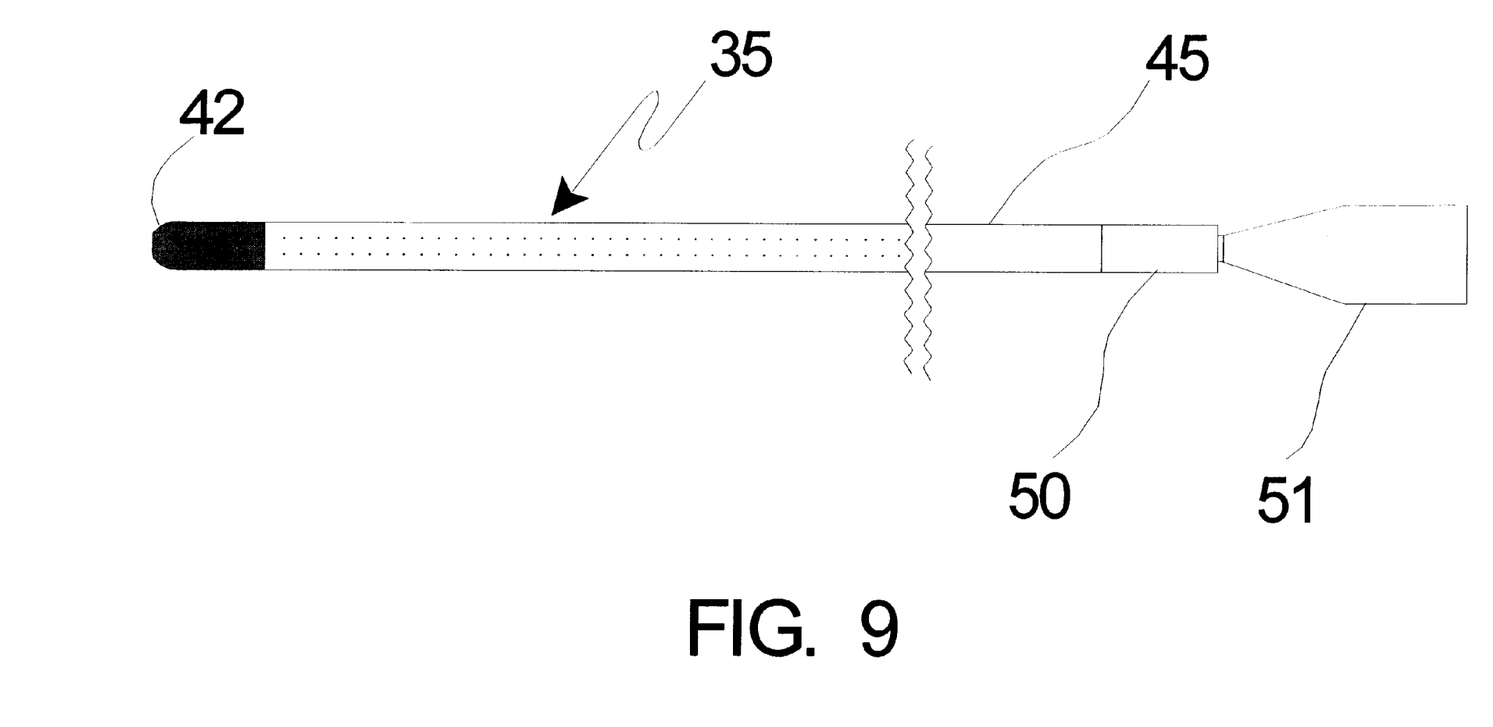
FIG. 9 is an axial view in side elevation showing the device of FIG. 8.

A three-in-one drainage device 35 is illustrated in FIG. 8 (plan view) and FIG. 9 (side view). As shown, three individual double-lumen drainage devices 36, 37 and 38 defining perforations 39 are bonded to each other by thin, severable membranes 46, 47 which may be constructed of a bio-compatible polymer such as, but not limited to PVC or silastic rubber. Each of the individual drainage devices 36, 37 and 38 are essentially the same as the single, double-lumen device 10 shown in FIG. 1.

Figure 10:
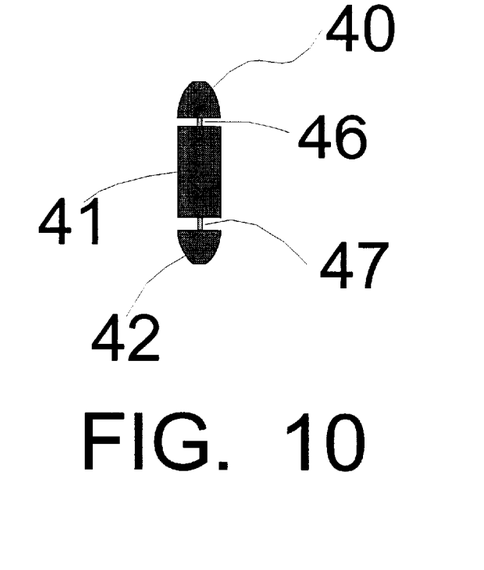
FIG. 10 is a reduced view in axial section taken along lines 10—10 of FIG. 8.
Figure 11:
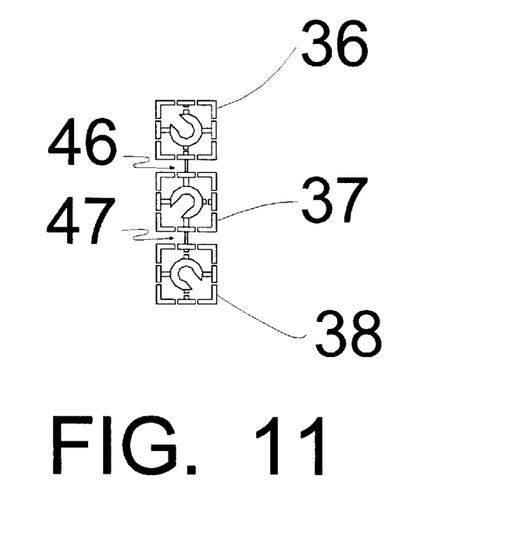
FIG. 11 is a reduced view in axial section taken along lines 11—11 of FIG. 8.
Figure 12:
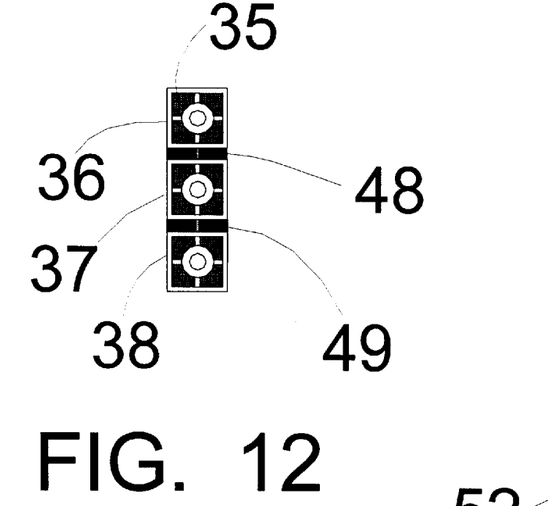
FIG. 12 is a reduced view in axial section taken along lines 12—12 of FIG. 8; and, FIG. 13 is a reduced view in axial section taken along lines 13—13 of FIG. 8.
Figure 13:
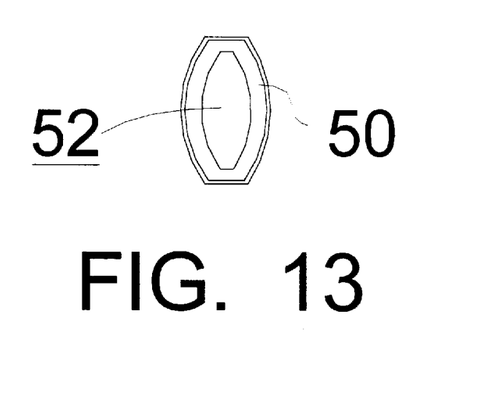

As shown in FIGS. 8 and 10, the distal ends 40, 41 and 42 of the three individual drainage devices form a flattened elliptical shape to facilitate entry into a patient's chest; the drainage devices define the proximal ends 43, 44 and 45. Spaces between the three individual tubes at the proximal end are filled with solid filling materials 48 and 49 (FIG. 12) such as polypropylene which function to provide rigidity between the inner and outer tubes. As shown in FIGS. 9 and 13, the three individual drainage devices 36, 37 and 38 are integrated together at the proximal ends of the device to form a single tube 50 with a single central suction bore 52 which is attached to a suction connector 51.

The double-lumen drainage device in both single and multiple-connected form provides a unique and useful product for post-operative situations, particularly lung surgery where long term chest drainage is required with a minimum of complications.

What is claimed is:

1. A double-lumen chest cavity drainage tube comprising:
   a.) a longitudinal, flexible, polymeric, perforated hollow inner tube constructed for connection to a suction source which produces sufficient suction to remove unwanted material from the chest cavity;
   b.) a longitudinal, flexible, polymeric, perforated hollow outer tube surrounding the inner tube and connected thereto, a circumferential, longitudinal space being defined along and between the inner and outer tubes, the perforations of the outer tube being substantially greater in total overall surface area than the total overall surface area of the inner tube perforations;
   c.) a plurality of perforated, hollow septa being disposed in the longitudinal space for preventing collapse of the tubes when suction pressure is applied to the inner tube, and to reduce and equalize the pressure in the circumferential space between the outer and inner tubes; whereby, when the drainage tube is inserted into the chest cavity and suction pressure is applied to the inner tube, suction forces produced in the circumferential space between and along the inner and outer tubes are reduced and equalized, the reduced suction forces then being uniformly applied to the individual outer tube perforations, the suction forces along the outer tube perforations consequently being reduced compared to the suction forces along the individual inner tube perforations, thereby reducing the possibility of lung or soft tissues being sucked onto the drainage tube and blocking the perforations during a chest drainage procedure.

2. The drainage tube of claim 1, in which the ratio of total surface area of the inner tube perforations to the total surface area of the outer tube perforations is about ⅓.

3. The drainage tube of claim 2, in which the perforations of the outer tube and the perforations of the hollow septa are about equal in diameter.

4. The drainage tube of claim 3, in which the perforations of the outer tube and the perforations of the hollow septa are about 1–1½ mm in diameter.

5. The drainage tube of claim 1, in which the outer tube is square-shaped and the inner tube is round-shaped.

6. The drainage tube of claim 1, comprising a plurality of drainage tubes bonded together with severable membranes to form a multiple drainage device, the membranes being severable into individual drainage devices when installed in a chest cavity.

7. The drainage device of claim 6, including a common suction bore for the drainage tubes.

8. The drainage tube of claim 6, comprising three drainage tubes bonded together to form a multiple drainage device.

9. The drainage tube of claim 6, comprising two drainage tubes bonded together to form a multiple drainage device.

10. A method for removing unwanted material from a chest cavity, comprising, inserting a double-lumen drainage tube into the chest cavity during a chest drainage procedure, the drainage tube comprising:

a.) a longitudinal, flexible, polymeric, perforated hollow inner tube constructed for connection to a suction source which produces sufficient suction to remove the unwanted material;

b.) a longitudinal, flexible, polymeric, perforated hollow outer tube surrounding the inner tube and connected thereto, a circumferential, longitudinal space being defined along and between the inner and outer tubes, the perforations of the outer tube being substantially greater in total overall surface area then the total overall surface area of the inner tube perforations;

c.) a plurality of perforated, hollow septa being disposed in the longitudinal space for preventing collapse of the tubes when suction pressure is applied to the inner tube, and to reduce and equalize the pressure in the circumferential space between the outer and inner tube; the method comprising:

inserting the drainage tube into the chest cavity and applying suction pressure to the inner tube, to thereby produce reduced and equalized suction forces in the circumferential space between and along the inner and outer tubes, the reduced and equalized suction forces then being uniformly applied to the individual outer tube perforations, the suction forces along the outer tube perforations consequently being reduced compared to the suction forces along the individual inner tube perforations, thereby reducing the possibility of lung or soft tissues being sucked onto the drainage tube and blocking the outer tube perforations during the chest drainage procedure.

11. The method of claim 10, in which the ratio of total surface area of the inner tube perforations to the total surface area of the outer tube perforations is about ⅓.

12. The method of claim 10, in which the perforations of the outer tube and the perforations of the hollow septa are about equal.

13. The method of claim 10, in which the perforations of the outer tube and the perforations of the hollow septa are about 1–1½ mm in diameter.

14. The method of claim 10, in which the outer tube is square-shaped, and the inner tube is round-shaped.

15. The method of claim 10, comprising employing a plurality of drainage tubes bonded together with severable membranes to form a multiple drainage device, the membranes being severable into individual drainage devices when installed in a chest cavity.

16. The method of claim 15, including a common suction bore for the drainage tubes.

17. The method of claim 15, comprising three drainage tubes bonded together to form a multiple drainage device.

18. The method of claim 15, comprising two drainage tubes bonded together to form a multiple drainage device.

\* \* \* \* \*